United States Patent [19]

Bjornson

[11] 4,331,566

[45] May 25, 1982

[54] CATALYST FOR HYDRODEALKYLATION PROCESS

[75] Inventor: Geir Bjornson, Bartlesville, Okla.

[73] Assignee: Phillips Petroleum Company, Bartlesville, Okla.

[21] Appl. No.: 232,058

[22] Filed: Feb. 5, 1981

Related U.S. Application Data

[60] Continuation of Ser. No. 66,585, Aug. 14, 1979, abandoned, which is a division of Ser. No. 902,651, May 4, 1978, Pat. No. 4,191,844.

[51] Int. Cl.$^3$ .................. B01J 21/04; B01J 21/12; B01J 23/78; B01J 23/84
[52] U.S. Cl. ........................ 252/466 J; 252/455 R
[58] Field of Search .......... 252/455 R, 466 PT, 466 J, 252/471

[56] References Cited

U.S. PATENT DOCUMENTS

| | | | |
|---|---|---|---|
| 2,514,960 | 7/1950 | Luten, Jr. et al. | 568/805 |
| 3,204,007 | 8/1965 | Mukai et al. | 585/402 |
| 3,284,513 | 12/1962 | Dedinas et al. | 585/489 |
| 3,597,491 | 8/1971 | Kovach et al. | 585/485 |
| 3,692,846 | 9/1972 | Dalman et al. | 585/489 |
| 3,700,745 | 10/1972 | Kovach et al. | 585/485 |
| 3,748,282 | 7/1973 | Evans | 585/485 |
| 3,751,505 | 8/1973 | Bergomi | 585/485 |
| 3,790,642 | 2/1974 | Kominami et al. | 585/485 |
| 3,919,339 | 11/1975 | Ransley | 585/481 |
| 3,963,602 | 6/1976 | Wright et al. | 585/485 |
| 3,966,833 | 6/1976 | Cosyns et al. | 585/489 |
| 3,992,468 | 11/1976 | Cosyns et al. | 585/489 |

Primary Examiner—W. J. Shine

[57] ABSTRACT

Hydrodealkylation of alkyl-substituted aromatic compounds by contacting with hydrogen in the presence of a catalyst of manganese oxide and a Group IIA metal oxide such as magnesium oxide, optionally promoted with a Group VIII hydrogenation metal such as nickel oxide and an alumina-containing isomerization component.

16 Claims, No Drawings

CATALYST FOR HYDRODEALKYLATION PROCESS

This application is a continuation of copending application Ser. No. 66,585, filed Aug. 14, 1979, now abandoned which is a division of application Ser. No. 902,651, filed May 4, 1978, now U.S. Pat. No. 4,191,844.

This invention relates to the use of a catalyst for the hydrodealkylation of aromatic compounds. In accordance with one aspect, this invention relates to the hydrodealkylation of alkyl-substituted aromatic compounds by contacting with a manganese oxide-Group IIA metal oxide catalyst. In accordance with another aspect, this invention relates to the hydrodealkylation of alkyl-substituted aromatic compounds by contacting with a manganese oxide-Group IIA metal oxide catalyst promoted with a Group VIII hydrogenation metal such as nickel oxide. In accordance with a further aspect, this invention relates to the hydrodealkylation of aromatic compounds by contacting with a manganese oxide-Group IIA metal oxide catalyst promoted with an alumina-containing isomerization component. In accordance with a further aspect, this invention relates to the hydrodealkylation of alkyl-substituted aromatic compounds by contacting with a manganese oxide-Group IIA metal oxide, e.g., magnesium oxide, promoted with a Group VIII metal, e.g., nickel oxide, and alumina-containing isomerization component, e.g., alumina or silica-alumina.

With the advent of increased coal production to help satisfy some of the current energy needs, there has been a correspondingly increased interest in coal as an alternate source for various chemicals such as phenol, cresols, xylenols, benzene, toluene, etc. Many so-called hard coals such as anthracite will continue to find application in the production of coke and as a heat fuel, but many other "intermediate" coals, low in heat value and mechanical properties such as lignite, will become prime sources for these sought-after chemicals.

Phenol is an important chemical product that can be derived from coal. It is important mainly because of its varied ones. One of the most important reactions of phenol which requires the greatest consumption is its condensation with formaldehyde to produce phenolic resins, an engineering plastic noted for its heat resistance useful in the appliances and electrical industries. Phenol can be condensed with acetone to form 4,4'-isopropylidenediphenol (bisphenol A), an intermediate for many epoxy resins. Phenol is also used to prepare such useful products as phenolphthalein, salicyclic acid, azo dyes, and monomers such as caprolactam leading to nylon-6.

Substituted phenols such as cresols and xylenols also have useful applications. Cresols find utility in disinfectants while 2,6-xylenol is used as a monomer for modified phenylene oxide polymers.

Coal tar, a condensable distillation product from coal carbonization or coke formation, was for many years the only source of phenol which has since been replaced by synthetic methods based on benzene and toluene. Cresols and xylenols are also derived from coal tars and petroleum. Cresols and xylenols have the same chemical structure as phenol except they have an added one or two methyl groups attached to the aromatic ring. Demethylation or dealkylation of cresols or xylenols to the more useful phenol thus appears to be an alternate synthetic method of preparation.

Accordingly, an object of this invention is to provide an improved process for the hydrodealkylation of aromatic compounds.

Another object of this invention is to provide improved catalysts useful for hydrodealkylation of aromatic compounds.

A further object of this invention is to provide a catalyst whereby the hydrodealkylation reaction can be carried out at a lower temperature than normally.

Another object of this invention is to provide a catalyst exhibiting isomerization activity useful for the treatment of isomers having nonreactive sites for hydrodealkylation.

Other objects, aspects, and the several advantages of the invention will be apparent to those skilled in this art upon a study of this disclosure and the appended claims.

According to the invention, alkyl-substituted aromatic compounds are hydrodealkylated in good selectivity and good conversion by contacting with hydrogen in the presence of a catalyst system containing manganese oxide and a Group IIA metal oxide and which can be optionally promoted with a Group VIII metal oxide and/or an alumina-containing material.

In accordance with one embodiment, alkyl-substituted aromatic compounds are hydrodealkylated in the presence of hydrogen and a catalyst system consisting essentially of manganese oxide and a Group IIA metal oxide such as magnesium oxide. The manganese/Group IIA metal portion of the catalyst is particularly useful with hydroxy-substituted alkyl aromatics such as cresols and xylenols and is considered to be selective because it allows disproportionation and dealkylation to occur at the ortho and para positions of the aromatic ring but not at the meta position.

In accordance with another embodiment, alkyl-substituted aromatic compounds are hydrodealkylated in the presence of hydrogen and a catalyst consisting essentially of manganese oxide, a Group IIA metal oxide such as magnesium oxide, and a Group VIII metal oxide, preferably an iron group metal oxide such as nickel oxide. The Group VIII metal oxide such as nickel oxide allows the dealkylation to occur at a lower temperature.

In accordance with a further embodiment, alkyl-substituted aromatic compounds are hydrodealkylated in the presence of hydrogen and a catalyst consisting essentially of manganese oxide, a Group IIA metal oxide and an alumina-containing isomerization component such as alumina or silica-alumina containing a major amount of alumina with or without a Group VIII metal oxide present in the catalyst. The presence of an alumina-containing material allows isomerization to occur from the nonreactive meta position to the reactive ortho position of an alkyl-substituted aromatic compound.

Further, in another embodiment of the invention, the invention provides a novel catalyst system based on oxides of manganese, Group IIA metals such as magnesium with or without a Group VIII metal oxide and an alumina-containining material which can be used to hydrodealkylate toluene, ethylbenzene, cresols, xylenols, and the like.

Any known method can be used for preparing the catalysts of this invention. The manganese and Group VIII, e.g., nickel, portion of the catalyst, for example, can be deposited on the Group IIA, e.g., magnesium oxide, carrier through impregnation by an aqueous solution of manganese or nickel nitrate. Alumina and/or silica-alumina can be present with the Group IIA magnesium oxide or can be employed as a separate contact zone proceding the dealkylation catalyst contact zone since its role is that of isomerization which can occur before or during dealkylation. The hydrated catalyst is then dried, preferably under vacuum, followed by calcining with air or nitrogen or mixtures thereof at 204° C., followed by a subsequent heating at about 400° C. for 30 minutes in the presence of hydrogen. Hydrogen reduces the metal oxide to its lowest possible valence state to prevent a similar reduction to occur in situ during the subsequent hydrodealkylation step. The initial heating or activation of these nitrate-type catalysts should be done outside the reactor because of the nitrous and nitric acids formed that can be harmful to the metal reactor or metal packing. Thereafter, the catalyst can be regenerated in the hydrodealkyklation reactor by passing nitrogen, air, or mixtures thereof over the catalyst. The amount of manganese oxide deposited on the Group IIA metal oxide, e.g., magnesium oxide, can be broadly 1 to 35 weight percent of the total catalyst system, but it is preferred to be about 3 to 25 weight percent. The particle size of the Group IIA metal oxide carrier can be any size convenient, but it is preferred in the current invention to be less than 50 mesh as measured by a U.S. Standard sieve screen.

The amount of optional Group VIII metal oxide, e.g., nickel oxide, deposited on the Group IIA metal oxide can be broadly 1 to 25 weight percent of the total catalyst system, but it is preferred to be about 2 to 10 weight percent.

Any type alumina can be used, but alpha-alumina is preferred. The alumina component can be accompanied by other ingredients such as silica so long as the additional ingredient is not harmful to the desired reaction and alumina is the major component. The optionally employed alumina-containing support can be blended with the Group IIA oxide carrier and can be present from 1 to 50 weight percent of the Group IIA oxide support although 5 to 20 weight percent is preferred.

The exact chemical identity of the manganese portion of the inventive catalyst is not known but is thought to occur as follows:

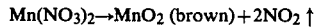

When the catalyst is used with hydrogen, it turns from brown to gray with the loss of water, indicating more reduction of the catalyst. It is thought the manganese is in a valence state less than +4 and greater than or equal to +2.

The feed for contacting according to the invention can comprise at least one substituted aromatic compound having at least one of alkyl and hydroxy substituents and includes aromatic compounds that are monocyclic as well as polycyclic. In general, the feed can be any substituted aromatic having either of the general formulas shown below:

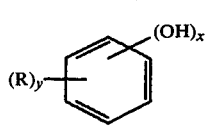 or 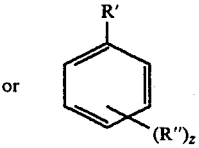

I  II wherein x is 1 to 3, y is 1 to 5, z is 0 to 5, and the sum of x and y is 2 to 6. R and R' are any alkyl radicals from 1 to 6 carbon atoms. R" is hydrogen or any alkyl or cycloalkyl radical from 1 to 6 carbon atoms.

Representative examples of materials that can be used corresponding to the general formula I include cresols (ortho, meta, para substituted), xylenols (2,3-; 2,4-; 2,5-; 2,6-; 3,4-; 3,5-), trimethylphenols, and the like, and mixtures thereof. Representative examples of materials that can be used corresponding to the general formula II include toluene, xylene, mesitylene, durene, p-cymene (1-methyl-4-isopropylbenzene), ethylbenzene, propylbenzene, cumene (isopropylbenzene), and the like, and mixtures thereof.

Solvents can be used if so desired and can be, for example, alkanes (e.g., hexane), or aromatic hydrocarbons, preferably benzene.

Hydrogen is co-mixed with the feed and should be in a slight molar excess, preferably about 1.5 moles of hydrogen to 1.0 mole of alkylated aromatic compound (e.g., cresol). Hydrogen helps prevent unwanted condensation reactions which can lead to coke formation.

Nitrogen with a small amount of hydrogen (e.g., 0.20 moles hydrogen/1.0 mole cresol) can be used if disproportionation is the desired reaction and not dealkylation. Dealkylation requires a molar excess of hydrogen which is used in part to form some of the dealkylation products (e.g., methane). On the other hand, disproportionation involves a mere transfer of an alkyl group from one position on the aromatic ring to another position and thus does not need hydrogen for any chemical reaction. Nevertheless, a small amount of hydrogen is used in disproportionation reactions to keep the preferred manganese oxide/magnesium oxide catalyst in a reduced state. The following equations using ortho cresol illustrate typical dealkylation and disproportionation reactions:

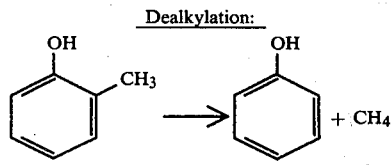

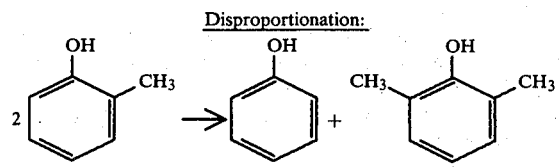

The reaction conditions of temperature and pressure used in carrying out the instant invention can vary appreciably depending upon the feed and catalyst composition but generally will be sufficient to effect at least one of dealkylation and dehydroxylation and produce dealkylated and dehydroxylated products. In accordance with specific embodiments of the invention, the conditions of reactions described herein differ with the total catalyst system used and are as follows:

| | Broad Range | Preferred Range |
|---|---|---|
| I. Manganese Oxide/Magnesium Oxide (Group IIA metal oxide) | | |
| Temperature, °F. | 700–1050 | 800–1000 |
| °C. | 371–565 | 427–538 |

-continued

|  | Broad Range | Preferred Range |
|---|---|---|
| Pressure, psig | 0–1000 | 10–700 |
| MPa | 0–6.89 | 0.0689–4.83 |
| II. Manganese Oxide/Magnesium Oxide (Group IIA metal oxide)/Nickel Oxide (Group VIII metal oxide) with or without Alumina | | |
| Temperature, °F. | 500–900 | 600–800 |
| °C. | 260–482 | 316–427 |
| Pressure, psig | 0–500 | 10–250 |
| MPa | 0–3.45 | 0.0689–1.72 |

Any type of reactor, but preferably a tubular reactor of stainless steel (e.g., 316) construction, can be employed. The walls of the reactor should be free of material which will interfere with the catalyzed reaction described herein. If desired, the catalyst can be positioned in the reactor near the middle or admixed with noncatalytic material such as quartz chips or stainless steel (i.e., 316) in order to effect better mixing and to reduce temperature gradients therein. Basically, the dried catalyst is placed in the reactor chamber with a bed of inert noncatalytic material above and below and heated to activation temperature while a mixture of nitrogen and air passes through the system. In the examples, the run begins by pressuring the preheated (ca 50° C.) feed through a filter into a Lapp pump and into the top mixing portion of the reactor zone. A static "o" ring switch is set about 100 psig, 0.680 MPa above the operating pressure of the system to protect the pump. Hydrogen is pressured through a Moore back-pressure regulator, heated, and mixed with the feed just before entering the mixing head. The hydrogen-feed mixture is passed through the reactor and through a steam-jacketed condenser and Moore back-pressure regulator into a chilled receiver. The products can then be analyzed and later separated usually by distillation.

The following examples serve to illustrate the operability of the current invention.

Examples II through VIII relate to the use of manganese oxide/magnesium oxide catalyst used to dealkylate hydroxyl-substituted aromatics such as cresol and xylenols and the selectivity associated with this catalyst system. Example I is a control catalyst of manganese oxide on alumina.

Examples IX through XIV relate to the use of manganese oxide/magnesium oxide catalyst to which has been added at least one of nickel oxide and alumina; the nickel oxide added to provide a similar dealkylation of hydroxylated aromatics but at a lower temperature and the alumina added to provide for isomerization from nonreactive sites on the aromatic ring to reactive sites.

Example XV relates to the use of manganese oxide/magnesium oxide catalyst used to dealkylate alkyl-substituted aromatic hydrocarbons such as toluene and ethylbenzene.

EXAMPLE I

A control catayst system based on manganese oxide on an alumina support was prepared as follows: gamma-alumina (one-eighth inch size, R-9850), 116 grams, was mixed with an aqueous solution of 3 grams potassium permanganate in 50 milliliters of water and vacuum dried at 25° to 50° C./1 mm. To this dried catalyst was added another aqueous solution of 0.65 grams potassium hydroxide (86%) in 40 milliliters of water and the combined mixture dried at about 25° to 50° C./1 mm. The dried catalyst was calcined at about 204° C. while a mixture of 40 percent air and 60 percent nitrogen was passed over the surface. The temperature was raised to about 315° C. to 371° C. to complete decomposition of potassium permanganate. The catalyst thus prepared contained 1.4 weight percent manganese dioxide on alumina. After placing in the tubular reactor, the catalyst was activated by heating to 426° C. for 30 minutes in the presence of hydrogen.

EXAMPLE II

This example describes the preparation of the inventive catalyst system, manganese oxide on magnesium oxide. Grace SMR 7-4938 magnesium oxide pellets (0.187 inch, 0.476 cm diameter size) was mechanically ground to allow passage through a 270-mesh size screen. To 59.1 grams of this sieved material was added 115 milliliters of water and 29.6 milliliters of a 50 weight percent aqueous solution of manganese nitrate. The paste-like material was mixed in a mortar and pestle, dried in an evaporating dish under vacuum 25° C. to 50° C./1 mm. The dried catalyst was calcined at about 204° C. while a mixture of 40 percent air and 60 percent nitrogen was passed over the surface. The temperature was raised to about 315° C. to 371° C. to complete decomposition of the manganese nitrate to manganese oxide. The catalyst thus prepared contained 15.8 weight percent manganese dioxide on magnesium oxide. The catalyst was then activated by heating at 426° C. for 30 minutes in the presence of hydrogen while in the tubular reactor.

EXAMPLE III

To a 316 stainless steel tubular reactor as herein described and having the dimensions 2.44 cm (0.960 in.) diameter by 70.49 cm (27.75 in.) was charged 60 milliliters of the catalyst system described in Example I. While the temperature was maintained at 482° C. (900° F.) and the pressure at 3.44 MPa (500 psi), an equimolar mixture of ortho, meta, and para cresol was fed through the reactor at a rate of about 55 to 60 milliliters per hour (1.0 LHSV), the pressure being maintained by hydrogen which mixes with the feed at a molar ratio of about 1.5 moles of hydrogen to 1.0 mole of cresol. The effluent product was analyzed without further separation with a Bendix ® 2300 chromatograph employing a column comprised of 12 weight percent 6-ringed polyphenyl ether on Chromasorb G, 80–100 mesh, which had been previously acid washed and dimethylsiliconized. The column was programmed as follows: 100° C. to 190° C. at 30° C./min.; 190° C. to 250° C. at 10° C./min.; and isothermal at 250° C. until complete. The run was repeated, and the analysis showed an average conversion of 26.5 percent with a product selectivity of 10.3 percent BTX (benzene, toluene, xylene), 50.9 percent phenol, and 38.9 percent xylenols. The run was repeated three times at 498° C. (930° F.) and once at 521° C. (970° F.) and analyzed as described. The average conversion at 498° C. was 43.7 percent (9.9% BTX, 56.0% phenol, 33.4% xylenols, and 0.7% trimethylphenol) and at 521° C., 51 percent (13.0% BTX, 62.1% phenol, 24.4% xylenols, and 0.4% trimethylphenol). At 521° C. the catalyst began to contain significant amounts of coke after a few hours operation.

EXAMPLE IV

The run described in Example III was twice repeated at 493° C. (920° F.) except the cresol feed contained eight weight percent water. Average analysis of the products after one hour operation was found to show 47.4 percent conversion with a product selectivity of 14.5% BTX, 62.1% phenol, and 23.1% xylenols. Water, added to the feed to aid in coke removal, had no effect on yields, conversion, product distribution, or catalyst activity.

EXAMPLE V

To a 316 stainless steel tubular reactor herein described was charged 60 milliliters of the catalyst system described in Example II, namely, manganese oxide on magnesium oxide. After the appropriate activation, a feed comprised of equimolar quantitites of ortho, meta, para cresol and eight weight percent water was passed through the catalyst bed as herein described at three different temperatures and at 500 psi. Analysis of the products from these three runs are shown in Table I below.

TABLE I

Cresol over Manganese Oxide/Magnesium Oxide

| Reaction Temperature | | % Conversion | % Selectivity | | |
|---|---|---|---|---|---|
| °C. | °F. | | BTX[b] | Phenol | Xylenols |
| 496[a] | 925 | 53.6 | 7.1 | 62.9 | 28.8 |
| 501 | 935 | 48.9 | 6.3 | 63.2 | 30.1 |
| 504 | 940 | 52.9 | 7.4 | 65.6 | 26.0 |

[a]Average of two runs.
[b]BTX = benzene, toluene, xylene.

EXAMPLE VI

The run described in Example V was repeated at three different temperatures but without water in the feed. Analysis was as shown below.

TABLE II

Effect of Temperature

| Reaction Temperature | | % Conversion | % Selectivity | | |
|---|---|---|---|---|---|
| °C. | °F. | | BTX | Phenol | Xylenols |
| 437 | 820 | 25.5 | 1.7 | 55.4 | 42.9 |
| 468 | 875 | 42.0 | 4.7 | 56.6 | 38.2 |
| 498 | 930 | 49.7 | 9.6 | 60.4 | 29.4 |

EXAMPLE VII

The run described in Example V was again repeated but at 498° C. (930° F.) at various lower pressures and with the separate isomers. Analysis of these runs is shown as follows:

EXAMPLE VIII

The run described in Example V was again repeated except the feed was comprised of 50 weight percent 2,5-xylenol (2,5-dimethylphenol) dispersed in 50 weight percent benzene passed through the reactor and catalyst at 498° C. (930° F.) and 3.45 MPa (500 psi) as herein described. Analyses of products from this run show a 58.4 weight percent conversion with the following product selectivity:

TABLE IV

| BTX | 6.7 |
|---|---|
| Phenol | 0.7 |
| o-Cresol | 1.3 |
| m-Cresol | 45.1 |
| 2,3-Xylenol | 15.3 |
| 2,6-Xylenol | 0.3 |
| 3,4-Xylenol | 4.4 |
| 3,5-Xylenol | 0 |
| 2,3,6-Trimethylphenol | 20.8 |
| 2,4,5-Trimethylphenol | 5.4 |

From these analyses it is calculated that 55 percent of the reaction is disproportionation and 45 percent is demethylation.

EXAMPLE IX

A control catalyst system based on nickel oxide on alumina support was prepared as follows: Zinc aluminate (ZnAl$_2$O$_4$), 80 grams, was impregnated with 40 milliliters of a solution which contained 20.6 grams of nickel nitrate, Ni(NO$_3$)$_2$.6H$_2$O, and the resulting paste dried and prepared for use as a catalyst in the same manner as described in Example I.

EXAMPLE X

This example describes the preparation of the inventive catalyst system, manganese oxide/magnesium oxide/nickel oxide. A solution was prepared comprised of 23.4 grams (0.13 moles) of manganese nitrate and 53.4 milliliters of water. Another solution was prepared by dissolving 9.50 grams (0.03 moles) nickel nitrate, Ni(NO$_3$)$_2$.6H$_2$O in 50 milliliters of water. The two solutions were mixed together and poured with stirring over 40.9 grams of powdered magnesium oxide (Fisher Chemical Co., M-51). The paste was spread into a 15.24 cm (6 in.)×0.32 cm (0.125 in.)×0.32 cm (0.125 in.) mold. The catalyst was allowed to dry at ambient room temperature for 16 to 24 hours. The catalyst was removed, broken into small pieces and calcined in a quartz or glass tube with a 50:50 volume percent air and nitrogen, first at 316°–371° C. (600°–700° F.) to remove oxides of nitrogen, then at 482°–510° C. (900°–950° F.). An alternate method of removing water and nitrogen oxides is to put the catalyst in a vacuum oven (<10 mm

TABLE III

Effect of Manganese Oxide/Magnesium Oxide Catalyst on the Conversion of Individual Cresol Isomers

| Feed | Pressure | | % Conversion | % Selectivity | | | | |
|---|---|---|---|---|---|---|---|---|
| | MPa | psi | | BTX | Phenol | Xylenols | | | 2,4,6-Trimethylphenol |
| | | | | | | 2,4- | 2,5- | 2,6- | |
| o-cresol | 0.34 | 50 | 42.6 | 0.7 | 54.1 | 4.8 | — | 39.4 | 1.1 |
| o-cresol | 3.45 | 500 | 50.3 | 3.3 | 54.5 | 11.9 | — | 27.3 | 2.8 |
| m-cresol | 0.17 | 25 | 2.5 | 65.5[a] | 30.9 | — | 3.7 | — | — |
| m-cresol | 0.34 | 50 | 2.4 | 69.3[b] | 30.7 | — | 0 | — | — |
| p-cresol | 0.17 | 25 | 18.0 | 1.6 | 54.4 | 40.3 | — | — | — |

[a]100% toluene.
[b]98.8% toluene, 1.2% xylene.

pressure) for 16-24 hours at 204° C. (400° F.). Catalyst dried from either method was placed in the hydrodealkylation tubular reactor and heated to about 10° C. (50° F.) above the desired hydrodealkylation operating temperature while a stream of hydrogen, containing some nitrogen initially, was passed through the reactor. The catalyst was then considered to be activated.

EXAMPLE XI

The manganese oxide/magnesium oxide/nickel oxide catalyst prepared in Example X was mixed with an equal volume of alpha-alumina in a manner similarly described in Example X. The catalyst was dried and activated as herein described.

EXAMPLE XII

The run described in Example III was repeated except the feed was ortho cresol and the catalyst was nickel oxide on alumina (Example IX). A large amount of BTX is produced relative to the amount of phenol produced and the catalyst "cokes out".

TABLE V

| Catalyst | Temperature °C. | °F. | Pressure MPa | psi | % Conversion | % Selectivity BTX | Phenol | Xylenols | Others |
|---|---|---|---|---|---|---|---|---|---|
| NiO/Al$_2$O$_3$ | 371 | 700 | 0.86 | 125 | 36.0 | 42.8 | 38.9 | 12.1 | 6.2 |
| NiO/Al$_2$O$_3$ | 398 | 750 | 0.86 | 125 | 15.6 | 30.4 | 50.6 | 16.4 | 2.5 |

EXAMPLE XIII

The catalyst MnO$_x$/MgO/NiO described in Example X was used to dealkylate various cresol isomers according to the procedure outlined in Example III. The data shown below indicate that when NiO is added to the MnO$_x$/MgO catalyst system the reaction temperature can be reduced from 499° C. (930° F.) to about 371°–398° C. (700°–750° F.) and still maintain a high selectivity to phenol. In addition, the pressure can be reduced from 3.79 MPa (550 psi) to about 0.14 MPa (25 psi).

EXAMPLE XIV

The catalyst MnO$_x$/MgO/NiO/Al$_2$O$_3$ described in Example XI was used to dealkylate a mixture comprised of 66 weight percent m-cresol, 30 weight percent p-cresol, and 4 weight percent xylenols. In order to use the MnO$_x$/MgO/NiO catalyst system employed in Example XIII with any cresol and/or xylenol stream containing meta isomers, it is necessary to add an isomerization catalyst to the system to move alkyl groups (i.e., methyl) from the inactive meta position to the more active ortho position which can then be readily dealkylated. Alumina or silica-alumina are known isomerization catalysts and when added to the MnO$_x$/MgO/NiO herein described make for the current inventive catalyst system. Table VII below gives the results using the inventive catalyst.

TABLE VII

| | Feed: | 66 weight percent m-cresol 30 weight percent p-cresol 4 weight percent xylenols | | | | | | | |
|---|---|---|---|---|---|---|---|---|---|
| Catalyst | Temperature °C. | °F. | Pressure MPa | psi | % Conversion | % Selectivity BTX | Phenol | Xylenols | Others |
| 50:50 wt. ratio MnO$_x$/MgO/NiO plus: | | | | | | | | | |
| Alumina | 371 | 700 | 0.86 | 125 | 55.9 | 0.9 | 41.2 | 29.9 | 20.3[a] |
| Alumina | 398 | 750 | 1.21 | 175 | 63.4 | 2.9 | 40.0 | 31.1 | 22.8[a] |
| Silica-Alumina | 398 | 750 | 0.86 | 125 | 63.5 | 4.6 | 40.6 | 29.7 | 22.1[a] |
| Silica-Alumina | 398 | 750 | 1.38 | 200 | 58.0 | 2.2 | 40.1 | 32.4 | 23.1[a] |

[a]Essentially all ortho cresol.

EXAMPLE XV

The catalyst system MnO$_x$/MgO described in Example II was used to dealkylate alkyl-substituted aromatic hydrocarbons in a manner described in Example III. When toluene was used as the feed, the conversion was relatively low but the selectivity to benzene was high. When ethylbenzene was the feed, both conversion and selectivity were high. Some metal oxides such as calcium oxide should be avoided since they can contribute to undesired products. For example, when ethylbenzene is the feed, more xylenes than benzene are produced. When toluene is the feed, the reverse is true. This reversal of product selectivity from similar type feeds is not understood at this time. These results are illustrated in Table VIII.

TABLE VI

| | Catalyst: MnO$_x$/MgO/NiO | | | | | | | | |
|---|---|---|---|---|---|---|---|---|---|
| Feed | Temperature °C. | °F. | Pressure MPa | psi | % Conversion | % Selectivity BTX | Phenol | Xylenols | Others |
| 50:50 o,m-cresol | 499 | 930 | 0.17 | 25 | 75.5 | 6.2 | 75.5 | — | 18.7 |
| o-cresol | 398 | 750 | 0.86 | 125 | 27.4 | 3.2 | 80.8 | 13.9 | 3.2 |
| o-cresol | 371 | 700 | 0.86 | 125 | 21.0 | 2.2 | 88.4 | 9.3 | — |
| m-cresol | 499 | 930 | 0.17 | 25 | 5.0 | 56.6 | 42.1 | — | 1.3 |
| m-cresol | 427 | 800 | 0.68 | 100 | 1.9 | 41.9 | 58.1 | — | — |
| p-cresol | 499 | 930 | 0.17 | 25 | 23.3 | 21.6 | 45.6 | 32.8 | — |
| p-cresol | 499 | 930 | 3.44 | 500 | 63.4 | 34.7 | 34.1 | 18.4 | 12.6 |

TABLE VIII

| Catalyst | Feed | Pressure: 3.44 MPa 500 psi | | % Conversion | % Selectivity | | |
|---|---|---|---|---|---|---|---|
| | | Temperature °C. | °F. | | Unknown | Benzene | Xylenes |
| MnO$_x$/MgO | Toluene | 517 | 963 | 12.7 | 1.3 | 98.3 | 0.4 |
| MnO$_x$/MgO | Toluene | 562 | 1045 | 32.2 | 5.3 | 93.0 | 1.7 |
| MnO$_x$/MgO/CaO[a] | Toluene | 538 | 1000 | 15.2 | 1.2 | 96.3 | 2.5 |
| MnO$_x$/MgO | Ethyl benzene | 538 | 1000 | 61.6 | 1.4 | 81.1 | 17.5 |
| MnO$_x$/MgO/CaO[a] | Ethyl benzene | 538 | 1000 | 62.7 | 1.2 | 28.2 | 70.6 |

[a]Catalyst prepared according to Example II and comprised initially of 90 grams MgO, 44 g Mn(NO$_3$)$_2$, 12.6 grams Ca(NO$_3$)$_2$ · 4H$_2$O, and 344 grams H$_2$O.

The following tables summarize the cresol conversion data herein described:

TABLE IX

Summary
Catalyst: MnO$_x$/Al$_2$O$_3$
Feed: Equimolar mixture of o, m, p-cresol

| Example | Temperature °C. | °F. | Pressure MPa | psi | % Conversion | % Selectivity BTX[a] | Phenol | Xylenol |
|---|---|---|---|---|---|---|---|---|
| III-1 | 482 | 900 | 3.45 | 500 | 26.5 | 10.3 | 50.9 | 38.9 |
| III-2 | 498 | 930 | 3.45 | 500 | 43.7 | 9.9 | 56.0 | 33.4 |
| III-3 | 521 | 970 | 3.45 | 500 | 51.0[c] | 13.0 | 62.1 | 24.4 |
| IV[b] | 493 | 920 | 3.45 | 500 | 47.4 | 14.5 | 62.1 | 23.1 |

[a]BTX is benzene, toluene, xylene.
[b]Feed contains 8 weight percent water.
[c]Coke formation.

TABLE X

Summary
Catalyst: MnO$_x$/MgO
Feed: Equimolar mixture of o, m, p-cresol

| Example | Temperature °C. | °F. | Pressure MPa | psi | % Conversion | % Selectivity BTX | Phenol | Xylenol |
|---|---|---|---|---|---|---|---|---|
| V-1[a] | 496 | 925 | 3.45 | 500 | 53.6 | 7.1 | 62.9 | 28.8 |
| V-2[a] | 501 | 935 | 3.45 | 500 | 48.9 | 6.3 | 63.2 | 30.1 |
| V-3[a] | 504 | 940 | 3.45 | 500 | 52.9 | 7.4 | 65.6 | 26.0 |
| VI-1 | 437 | 820 | 3.45 | 500 | 25.5 | 1.7 | 55.4 | 42.9 |
| VI-2 | 468 | 875 | 3.45 | 500 | 42.0 | 4.7 | 56.6 | 38.2 |
| VI-3 | 498 | 930 | 3.45 | 500 | 49.7 | 9.6 | 60.4 | 29.4 |

[a]Feed contains 8 weight percent water.

TABLE XI

Summary
Effects of Nickel Oxide on Catalyst Activity of MnO$_x$/MgO

| Feed | Catalyst | Temperature °C. | °F. | Pressure MPa | psig | % Conversion | % Selectivity Phenol | BTX[b] | Xylenol | Others |
|---|---|---|---|---|---|---|---|---|---|---|
| o-cresol | NiO/Al$_2$O$_3$ | 398 | 750 | 0.86 | 125 | 15.6[a] | 30.4 | 50.6 | 16.4 | 2.5 |
| o-cresol | MnO$_x$/MgO | 499 | 930 | 3.79 | 550 | 49.9 | 62.5 | 6.3 | 30.6 | 0.4 |
| o-cresol + m-cresol | MnO$_x$/MgO/NiO | 499 | 930 | 0.17 | 25 | 75.5 | 75.5 | 6.2 | — | 18.7 |
| o-cresol | MnO$_x$/MgO/NiO | 398 | 750 | 0.86 | 125 | 27.4 | 80.8 | 3.2 | 13.9 | 3.2 |
| m, p-cresol[c] | 50% Al$_2$O$_3$ + 50% MnO$_x$/MgO/NiO | 398 | 750 | 1.21 | 175 | 63.4 | 40.0 | 2.9 | 31.1 | 22.8[d] |

[a]"Cokes out" at high reaction temperatures.
[b]BTX = benzene, toluene, xylene.
[c]66 Wt. % m-cresol, 30 wt. % p-cresol, 4 wt. % xylenols.
[d]Essentially o-cresol.

Summarizing the data herein disclosed, it is seen that the manganese oxide/magnesium oxide catalyst of the invention is selective, causing disproportionation and dealkylation to occur under the proper reaction conditions but little, if any, isomerization to occur. This is particularly apparent from the data in Table IV involving 2,5-dimethylphenol where most of the products obtained still retain substitution at the meta position. The data also show 55 percent of the reaction to be disproportionation and 45 percent to be dealkylation (demethylation).

The data from Table III again show the selectivity of the catalyst, with most activity in the ortho position, less activity in the para position, and almost no activity in the meta position. Again dealkylation predominates with slightly less disproportionation and no isomerization. The data also indicate the activity of the catalyst is good at very low pressures such as 0.17 MPa (25 psi).

The advantages of the manganese oxide/magnesium oxide catalyst of the invention over a similar catalyst system but with a different support, namely, manganese oxide/aluminum oxide can be seen in Tables I and II and summary Tables IX and X where an equimolar amount of ortho, meta, and para cresol is passed over the respective catalysts under various conditions. The manganese oxide/magnesium oxide catalyst of the invention produces slightly more phenol but more important significantly less BTX (benzene, toluene, and xylene) than with the control catalyst, manganese oxide on aluminum oxide. Unlike the xylenols, the BTX's cannot be recycled for subsequent conversion to phenol because they have lost the hydroxyl group. The catalyst of the invention permits the dealkylation-disproportionation reactions to occur at much lower temperatures (e.g., 437° C. to 498° C. versus 498° C. to 521° C. for the control) and consequently less coke formation occurs. Less coke formation suggests a longer catalyst life is possible with the inventive catalyst.

The $MnO_x/MgO$ catalyst of the invention gives a higher product conversion than the control catalyst when the reaction is carried out under the same reaction conditions. At 498° C. (930° F.) and 3.45 MPa (500 psi), the control catalyst gives a 43.7 percent conversion whereas the inventive catalyst gives a 49.7 percent conversion.

The data from Tables V, VI, VII, and XI (Summary) show that cresols can be converted in high selectivity to phenols and xylenols using the catalyst based on manganese, magnesium, nickel, and optionally with alumina, with very little production of dehydroxylated products which cannot be recycled (e.g., benzene). Nickel on alumina alone "cokes" and gives a large amount of benzene with a low cresol conversion but when manganese and magnesium are present, high conversion and high yields of hydroxy-substituted products are formed. The manganese/magnesium portion of the catalyst allows disproportionation and dealkylation to occur at the active ortho and less active para position of an aromatic ring but not at the meta position. The aluminum oxide allows isomerization of alkyl groups from the inactive meta position to the more active ortho or para position. The nickel allows the overall reaction to occur at lower temperatures and lower pressures.

I claim:
1. A catalyst consisting essentially of:
   (a) about 1-35 weight percent manganese oxide,
   (b) about 1-25 weight percent of a Group VIII metal oxide, and the balance being a mixture of
   (c) a Group IIA metal oxide carrier, and
   (d) a carrier containing alumina or silica-alumina containing a major amount of alumina.
2. A catalyst according to claim 1 wherein the amount of (d) ranges from about 1-50 weight percent based on the amount of (c) present in said catalyst.
3. A composition according to claim 2 wherein the amount of (a) present is in the range of about 3-25 weight percent, the amount of (b) is in the range of about 2 ∝ 10 weight percent, and the amount of (d) is in the range of about 5-20 weight percent based upon (c).
4. A catalyst according to claim 2 wherein
   (a) is manganese oxide,
   (b) is nickel oxide,
   (c) is magnesium oxide, and
   (d) is alumina.
5. A catalyst according to claim 4 wherein the amount of (a) present is in the range of about 3-25 weight percent, the amount of (b) present is in the range of about 2-10 weight percent, and the amount of alumina present ranges from about 5-20 weight percent of the magnesium oxide present in the catalyst.
6. A catalyst according to claim 1 wherein (b) is an iron group metal.
7. A catalyst according to claim 6 wherein (b) is nickel oxide.
8. A catalyst according to claim 6 wherein the amount of (d) ranges from about 1-50 weight percent based on the amount of (c) present in said catalyst.
9. A catalyst according to claim 8 wherein the amount of (a) present is in the range of about 3-25 weight percent, the amount of (b) present is in the range of about 2-10 weight percent, and the amount of alumina present ranges from about 5-20 weight percent of the Group IIA metal oxide present in the catalyst.
10. A catalyst according to claim 9 wherein (b) is nickel oxide.
11. A catalyst consisting essentially of:
    (a) about 1-35 weight percent manganese oxide,
    (b) about 1-25 weight percent nickel oxide, and
    (c) the balance a Group IIA metal oxide carrier.
12. A catalyst according to claim 11 wherein (c) is magnesium oxide.
13. A catalyst produced by a process which comprises the steps of:
    (1) depositing a manganese-containing component and a Group VIII metal-containing component from aqueous solution onto a carrier which comprises a mixture of a Group IIA metal oxide and alumina or silica-alumina containing a major amount of alumina;
    (2) drying the product of step (1);
    (3) calcining the product of step (2); and
    (4) reducing the product of step (3) to its lowest possible valence state.
14. The catalyst of claim 13 wherein the Group VIII metal employed in step (1) is nickel.
15. The catalyst of claims 13 or 14 wherein step (3) takes place in the presence of air, nitrogen, or mixtures thereof.
16. A catalyst produced by a process comprising the steps of:
    (1) admixing a solution of a manganese-containing component, a Group VIII metal-containing component, and a carrier component containing a mixture of a Group IIA metal oxide alumina or silica-alumina containing a major amount of alumina,
    (2) drying said admixture;
    (3) calcining the product of step (2) to produce a catalyst composition containing about:
    1-35 wt. % manganese oxide,
    1-25 wt. % Group VIII metal oxide, and the balance being a mixture of a Group IIA metal oxide and alumina or silica-alumina containing a major amount of alumina; and
    (4) reducing the product of step (3) in the presence of hydrogen to its lower possible valence state.

* * * * *

UNITED STATES PATENT AND TRADEMARK OFFICE
CERTIFICATE OF CORRECTION

PATENT NO. : 4,331,566
DATED : May 25, 1982
INVENTOR(S) : Geir Bjornson

It is certified that error appears in the above-identified patent and that said Letters Patent is hereby corrected as shown below:

Claim 3, line 4, "2$\alpha$10" should be ---2-10---.

*Signed and Sealed this*

*Sixth* Day of *December 1983*

[SEAL]

*Attest:*

GERALD J. MOSSINGHOFF

*Attesting Officer*     *Commissioner of Patents and Trademarks*